United States Patent [19]

Scharwaechter et al.

[11] 4,333,936
[45] Jun. 8, 1982

[54] NOVEL AMIDINO-BENZYLPYRIMIDINES, PROCESSES FOR THEIR MANUFACTURE AND ANTIBACTERIAL AND ANTIPROTOZOAL USE THEREOF

[75] Inventors: Peter Scharwaechter, Moorrege; Klaus Gutsche, Rellingen; Wilhelm Kohlmann, Moorrege, all of Fed. Rep. of Germany; Gerhard Kroemer, deceased, late of Elmshorn, Fed. Rep. of Germany; by Norma Kroemer, legal representative, Lahn-Giessen, Fed. Rep. of Germany; by Helmut Kroemer, legal representative; by Maria M. Kroemer, legal representative, both of Stolberg, Fed. Rep. of Germany

[73] Assignee: BASF Aktiengesellschaft, Fed. Rep. of Germany

[21] Appl. No.: 921,175

[22] Filed: Jul. 3, 1978

[51] Int. Cl.$^3$ ............... C07D 239/49; C07D 403/12; C07D 413/12; A61K 31/505

[52] U.S. Cl. .................................. 424/251; 424/228; 424/229; 260/243.3; 544/63; 544/96; 544/122; 544/238; 544/295; 544/296; 544/324; 544/325

[58] Field of Search ............... 544/324, 325, 238, 295, 544/296, 96, 63, 122; 424/251; 260/243.3

[56] References Cited

U.S. PATENT DOCUMENTS

Re. 28,636 12/1975 Grunberg ........................... 424/251
3,049,544  8/1962 Stehbuck et al. ................... 544/325

FOREIGN PATENT DOCUMENTS 336 1/1979 European Pat. Off. ............ 544/325

OTHER PUBLICATIONS

Nemeryuk et al., Chem. Abs. 82, 170830f, (1975).
Wollweber et al., Chem. Abs. 76, 72265g, (1971).

Primary Examiner—Mark L. Berch
Attorney, Agent, or Firm—Keil & Witherspoon

[57] ABSTRACT

5-Benzyl-4-amino-pyrimidine-2-amidines which may or may not be substituted in the phenyl ring, and their physiologically acceptable addition salts with acids, processes for their preparation, drugs containing these compounds, and their use in infectious diseases.

25 Claims, No Drawings

NOVEL AMIDINO-BENZYLPYRIMIDINES, PROCESSES FOR THEIR MANUFACTURE AND ANTIBACTERIAL AND ANTIPROTOZOAL USE THEREOF

The present invention relates to novel amidino-benzyl-pyrimidines of the general formula I

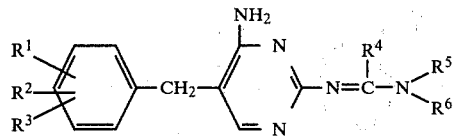

where $R^1$, $R^2$, and $R^3$, which may be identical or different, are hydrogen, methyl, methoxy or chlorine, $R^4$ is alkyl of 1 to 6 carbon atoms or benzyl and $R^5$ and $R^6$, which may be identical or different, are hydrogen, lower alkyl of 1 to 4 carbon atoms, substituted or unsubstituted benzyl or phenyl, cyclohexy, adamantyl or furfuryl, or one of the radicals $R^5$ and $R^6$ is —$C_6H_4SO_2$—NH—$R^7$, where $R^7$ is

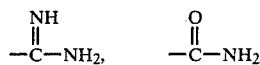

or a heterocyclic ring of 5–6 ring members, which contains from 1 to 3 hetero-atoms which may be identical or different from one another and are nitrogen or oxygen, and which may be substituted by chlorine, methyl or methoxy, or $R^5$ and $R^6$ together with the nitrogen to which they are bonded are a saturated heterocyclic ring of 5–7 members, which may contain an oxygen atom or the >N—Y group, where Y is methyl, benzyl or phenyl, and to their pharmacologically acceptable salts with acids conventionally used for this purpose.

Examples of conventional acids used to form pharmacologically acceptable salts are hydrochloric acid, nitric acid, sulfuric acid, phosphoric acid, acetic acid, lactic acid, citric acid and salicylic acid.

Preferably, the substituents $R^1$, $R^2$ and $R^3$ are in the 3-, 4- and 5-positions of the benzene ring.

Preferred compounds of the formula I are those where $R^4$ is lower alkyl of 1 to 4 carbon atoms or benzyl, and $R^5$ and $R^6$, which may be identical or different, are hydrogen, lower alkyl of 1 to 4 carbon atoms, benzyl or phenyl, or together are polymethylene of 4 to 5 methylene groups, which may be interrupted by oxygen or >N—Y, where Y is methyl, benzyl or phenyl, or $R^5$ is hydrogen and $R^6$ is —$C_6H_4$—$SO_2NH$—$R^7$, where $R^7$ is

or pyrimidin-2-yl, 4-methyl-pyrimidin-2-yl, 5-methyl-pyrimidin-2-yl, 5-isopropyl-pyrimidin-2-yl, 5-methoxy-pyrimidin-2-yl, 6-methoxy-pyridazon-3-yl, 3-methoxy-pyrazin-2-yl, 5-methyl-isoxazol-3-yl or 2-pyridinyl, and $R^1$, $R^2$ and $R^3$ have the same meanings as in formula I.

Amongst the above compounds of the formula I, more preferred compounds are those where $R^1$, $R^2$ and $R^3$ are hydrogen, methyl or methoxy, and amongst these, in turn, the compounds where $R^1$, $R^2$ and $R^3$ are in the 3-, 4- and 5-positions of the benzyl radical and are each methoxy are especially preferred.

The compounds of the formula I are anti-microbially active in illnesses caused by bacteria and protozoa and, when combined with sulfonamides, potentiate their antibacterial action. They may be used, for example, in bacterial infections of the respiratory organs, digestive organs and urinary tract, in infections of the throat, nose and ears, in systemic infections in general, and in malaria.

Examples of suitable sulfonamides are 2-sulfanilamido-pyridine, 2-sulfanilamido-thiazole, 2-sulfanilamido-pyrimidine, 2-sulfanilamido-4-methyl-pyrimidine, 2-sulfanilamido-4,6-dimethyl-pyrimidine, 4-sulfanilamido-2,6dimethyl-pyrimidine, 5-sulfanilamido-3,4-dimethyl-isoxazole, 3-sulfanilamido-6-methoxy-pyridazine, 3-sulfanilamido-6-chloro-pyridazine, 4-sulfanilamido-2,6-dimethoxy-pyrimidine, 3-sulfanilamido-2-phenyl-pyrazole, 2-sulfanilamido-5-methyl-pyrimidine, 2-sulfanilamido-5-methoxy-pyrimidine, 2-sulfanilamido-5-methyl-isoxazole, 2-sulfanilamido-4,5-dimethyloxazole, 2-sulfanilamido-3-methoxy-pyrazine, 4-sulfanilamido-5,6-dimethoxy-pyrimidine, 4-sulfanilamido-3-methoxy-1,2,5-thiadiazole and 4-amino-benzene-sulfonyl-guanidine.

The compounds of the formula I and their salts can be combined with the sulfonamides, mentioned by way of example, in various ratios; the ratio of the former to the latter may be from 1:10 to 5:1. However, preferred ratios are from 1:1 to 1:5. As a rule, a suitable dosage is from 20 to 550 mg of an active ingredient of the formula I.

The compounds according to the invention, of the formula I, are prepared by the conventional methods of preparing amidines, as described, inter alia, in Houben-Weyl, "Methoden der organischen Chemie," Volume 11/2, in which an imido-acid ester of the general formula II

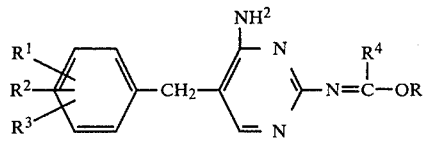

where $R^1$, $R^2$, $R^3$ and $R^4$ have the above meanings and $R^8$ is lower alkyl of 1 to 4 carbon atoms or benzyl, is reacted with an amine of the general formula III

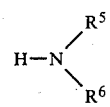

where $R^5$ and $R^6$ have the above meanings, to give the amidine of the general formula I

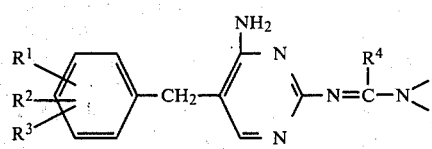

which then may or may not be converted to a pharmacologically acceptable addition salt with an acid conventionally used for this purpose.

The imido-acid esters of the general formula II and their preparation are described in our co-pending German patent application No. P 27 30 468.3 filed July 6, 1977. A corresponding patent application claiming this priority has also been filed in the country of the present application.

Examples of amines of the formula III are ammonia, methylamine, dimethylamine, diethylamine, benzylamine, 3,4,5-trimethoxybenzylamine, N-phenyl-piperazine, furfurylamine, cyclohexylamine, pyrrolidine, piperidine, morpholine and aniline, and sulfonamides, eg. 2-sulfanilamido-pyrimidine, 2-sulfanilamido-4-pyrimidine, 2-sulfanilamido-5-methyl-pyrimidine, 2-sulfanilamido-5-isopropyl-pyrimidine, 2-sulfanilamido-5-methoxy-pyrimidine, 3-sulfanilamido-6-methoxy-pyridazine, 2-sulfanilamido-3-methoxy-pyrazine, 3-sulfanilamido-5-methyl-isoxazole and 2-sulfanilamido-pyridine.

These compounds may be prepared in the presence or absence of a solvent. Examples of suitable solvents are pyridine, ethanol, water and mixtures of these solvents. The reaction temperatures are from 0° to 150° C., preferably from 20° to 120° C., or up to the boiling point of the solvent used.

If, for example, N-[4-amino-5-(3,4,5-trimethoxybenzyl)-pyrimidin-2-yl]-acetimido-acid ethyl ester and aniline are used as starting materials, the course of the reaction can be represented by the following equation:

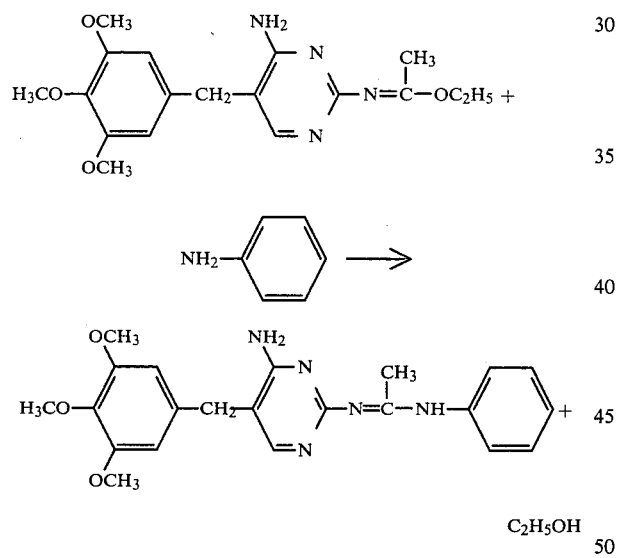

To demonstrate the action of the compounds according to the invention, the latter were tested in animal experiments, using the Aronson sepsis model, infection being carried out with *Streptococcus agalactiae*, and were compared with the conventional drug Trimethoprim. Groups of 30 female mice were infected with a lethal dose of *Streptococcus agalactiae* 7941 and 2 hours after infection were treated with a mixture of 300 mg of 2-sulfanilamido-4,5-dimethyloxazole + 60 mg of one of the compounds according to the invention. In addition to an untreated control group, a second group was treated with a mixture—serving as a reference substance—of 300 mg of 2-sulfanilamido-4,5-dimethyloxazole + 60 mg of trimethoprim. After 44 hours, the number of surviving animals was determined and divided by the number of survivors from the group treated with the reference substance. The numerical value thus obtained (the Trimethoprim factor) is a measure of the action of the compounds according to the invention compared to Trimethoprim. Accordingly, F = 2 means that the compound is twice as active as Trimethoprim. The Table which follows shows that the compounds according to the invention exhibit up to a 5.4-fold superiority over Trimethoprim.

TABLE

General formula $$\text{(trimethoxybenzyl-pyrimidine with } -N=C(R^4)-A \text{ substituent)}$$

| No. | $R^4$ | A | F |
|---|---|---|---|
| 1 | $CH_3-$ | $-N(CH_3)_2$ | 1,2 |
| 2 | $CH_3-$ | $-N\text{(piperazinyl)}-\text{phenyl}$ | 1,7 |
| 3 | $CH_3-$ | $-NH-\text{phenyl}$ | 1,2 |
| 4 | $CH_3-$ | $-NH-CH_2-\text{phenyl}$ | 1,3 |
| 5 | $CH_3-$ | $-NH-CH_2-\text{(3,4,5-trimethoxyphenyl)}$ | 1,0 |
| 6 | $CH_3-$ | $-NH-\text{C}_6\text{H}_4-SO_2-NH-\text{(pyrimidin-2-yl)}$ | 5,4 |
| 7 | $CH_3-$ | $-NH-\text{C}_6\text{H}_4-SO_2-NH-\text{(5-methoxypyrimidin-2-yl)}$ | 1,6 |
| 8 | $CH_3-$ | $-NH-\text{C}_6\text{H}_4-SO_2-NH-\text{(5-methylpyrimidin-2-yl)}$ | 5,1 |
| 9 | $CH_3-$ | $-NH-\text{C}_6\text{H}_4-SO_2-NH-\text{(4-methylpyrimidin-2-yl)}$ | 1,25 |
| 10 | $CH_3-$ | $-NH-\text{C}_6\text{H}_4-SO_2-NH-\text{(6-methoxypyridazin-3-yl)}$ | 1,0 |

Accordingly, the present invention also relates to chemotherapeutic agents which contain a compound of the formula I, in particular in combination with a sulfonamide, as the active ingredient, together with conventional carriers and excipients, and to the use of the compounds of the formula I as sulfonamide potentiators.

The chemotherapeutic agents or formulations are prepared in the conventional manner, using the conventional carriers or excipients and conventional pharmacological assistants, in accordance with the desired route of administration.

The preferred formulations are those suitable for oral administration. Examples are tablets, film tablets, dragees, capsules, pills, powders, solutions and suspensions.

EXAMPLE 1

16.2 g of N-[4-amino-5-(3,4,5-trimethoxybenzyl)-pyrimidin-2yl]-acetimido-acid ethyl ester are dissolved in 120 ml of pyridine, 14 ml of a saturated solution of ammonia in ethanol are added and the mixture is stirred for 12 hours at 70° C. After concentration under reduced pressure, the residue is recrystallized from dioxane. 8.6 g (57.7% of theory) of N-[4-amino-5-(3,4,5-trimethoxybenzyl)-pyrimidin-2-yl]-acetamidine of melting point 207° C. are obtained.

EXAMPLE 2

1.8 g of N-[4-amino-5-(3,4,5-trimethoxybenzyl)-pyrimidin-2-yl]-acetimido-acid ethyl ester, 0.93 g of aniline and 20 ml of absolute ethanol are refluxed for 15 hours whilst stirring and are then cooled, and 80 ml of water are added. 1.1 g (53% of theory) of N-[4-amino-5-(3,4,5-trimethoxybenzyl)-pyrimidin-2-yl]-N'-phenyl-acetamidine of melting point 189° C. are obtained.

EXAMPLE 3

1.8 g of N-[4-amino-5-(3,4,5-trimethoxybenzyl)-pyrimidin-2-yl]-acetimido-acid ethyl ester are stirred with 20 ml of 40 percent strength aqueous dimethylamine solution for 10 hours at 50°–60° C. The crystalline precipitate is filtered off, washed with water and recrystallized from dioxane. 1.24 g (69% of theory) of N-[4-amino-5-(3,4,5-trimethoxybenzyl)-pyrimidin-2-yl]-N',N'-dimethyl-acetamidine of melting point 220° C. are obtained.

EXAMPLE 4

Using the method described in Example 3, N-[4-amino-5-(3,4,5-trimethoxybenzyl)-pyrimidin-2-yl]-N',N'-diethylacetamidine of melting point 154° C. was obtained from N-[4-amino-5-(3,4,5-trimethoxybenzyl)-pyrimidin-2-yl]-acetamido-acid ethyl ester and diethylamine.

EXAMPLE 5

1.8 g of N-[(4-amino-5-(3,4,5-trimethoxybenzyl)-pyrimidin-2-yl]-acetimido-acid ethyl ester are suspended in 10 ml of N-phenylpiperazine and the mixture is heated at 65° C. until all has dissolved and is then stirred for 3 hours at 90°–100° C. After cooling, the mixture is treated with 100 ml of diethyl ether and the white crystalline precipitate is filtered off and recrystallized from butyl acetate. 1.6 g (67% of theory) of N-[(4-amino-5-(3,4,5-trimethoxybenzyl)-pyrimidin-2-yl]-N',N'-(3-aza-3-phenyl-pentamethylene)-acetamidine of melting point 197° C. are obtained.

EXAMPLE 6

Using the method described in Example 5, N-[4-amino-5-(3,4,5-trimethoxybenzyl)-pyrimidin-2-yl]-N',N'-tetramethylene-acetamidine of melting point 198° C. was prepared from N-[4-amino-5-(3,4,5-trimethoxybenzyl)-pyrimidin-2-yl]-acetimido-acid ethyl ester and pyrrolidine.

EXAMPLE 7

5.4 g of N-[4-amino-5-(3,4,5-trimethoxybenzyl)-pyrimidin-2-yl]-acetimido-acid ethyl ester and 1.6 g of benzylamine are dissolved in 40 ml of pyridine and the mixture is stirred for 2 hours at 90° C. After concentrating the mixture under reduced pressure, the residue is dissolved in 200 ml of warm ethyl acetate and the solution is clarified with active charcoal and cooled. 3.2 g (51% of theory) of N-[4-amino-5-(3,4,5-trimethoxybenzyl)-pyrimidin-2-yl]-N'-benzyl-acetamidine of melting point 164° C. crystallize from the solution.

The following were prepared by the method described in Example 7:

8. N-[4-Amino-5-(3,4,5-trimethoxybenzyl)-pyrimidin-2-yl]-N'-(3,4,5-trimethoxybenzyl)-acetamidine of melting point 143° C. from N-[4-amino-5-(3,4,5-trimethoxybenzyl)-pyrimidin-2-yl]-acetimido-acid ethyl ester and 3,4,5-trimethoxybenzylamine.

9. N-[4-Amino-5-trimethoxybenzyl)-pyrimidin-2-yl]N',N'-(3-oxa-pentamethylene)-acetamidine of melting point 205° C. from N-[4-amino-5-(3,4,5-trimethoxybenzyl)-pyrimidin-2-yl]-acetimido-acid ethyl ester and morpholine.

10. N-[4-Amino-5-(3,4,5-trimethoxybenzyl)-pyrimidin-2-yl]-N'-furfuryl-acetamidine of melting point 184° C. from N-[4-amino-5(3,4,5-trimethoxybenzyl)-pyrimidin-2-yl]-acetimido-acid ethyl ester and furfurylamine.

11. N-[4-Amino-5-(3,4,5-trimethoxybenzyl)-pyrimidin-2-yl]-N'-cyclohexyl-acetamidine of melting point 183° C. from N-[4-amino-5-(3,4,5-trimethoxybenzyl)-pyrimidin-2-yl]-acetimido-acid ethyl ester and cyclohexylamine.

12. N-[4-Amino-5-(3,4,5-trimethoxybenzyl)-pyrimidin-2-yl]-N'-adamantyl-acetamidine of melting point 248° C. from N-[4-amino-5-(3,4,5-trimethoxybenzyl)-pyrimidin-2-yl]-acetimido-acid ethyl ester and 1-adamantylamine.

EXAMPLE 13

10.8 g of N-[4-amino-5-(3,4,5-trimethoxybenzyl)-pyrimidin-2yl]-acetimido-acid ethyl ester and 4.2 g of 2-sulfanilamido-5-methoxy-pyrimidine (sulfamethoxydiazine) are dissolved in 80 ml of pyridine and the reaction mixture is stirred for 12 hours under reflux and then concentrated under reduced pressure. After dissolving the residue in warm acetone and treating the solution with active charcoal, 5.43 g (60.8% of theory) of N-[4-amino-5-(3,4,5-trimethoxybenzyl)-pyrimidin-2-yl]-N'-[4-(5-methoxypyrimidin-2yl)-sulfonamido]-phenyl-acetamidine of melting point 218° C. crystallize out.

The following were prepared by the method described in Example 13:

14. N-[4-Amino-5(3,4,5-trimethoxybenzyl)-pyrimidin-2-yl]-N'-[4-(5-methyl-pyrimidin-2-yl)-sulfonamido]-phenyl-acetamidine of melting point 192° C. from N-[4-amino-5-(3,4,5-trimethoxybenzyl)-pyrimidin-2-yl]-acetimido-acid ethyl ester and 2-sulfanilamido-5-methyl-pyrimidine (sulfaperine).

15. N-[4-Amino-5-(3,4,5-trimethoxybenzyl)-pyrimidin-2-yl]-N'-[4-(pyrimidin-2-yl)-sulfonamido]-phenyl-acetamidine of melting point 178° C. (with decomposition) from N-[4-amino-5-(3,4,5-trimethoxybenzyl)-pyrimidin-2-yl]-acetimido-acid ethyl ester and 2-sulfanilamido-pyrimidine (sulfadiazine).

16. N-[4-Amino-5-(3,4,5-trimethoxybenzyl)-pyrimidin-2-yl]-N'-[4-(4-methyl-pyrimidin-2-yl)-sulfonamido]-phenyl-acetamidine of melting point 162° C. from N-[4-amino-5-(3,4,5-trimethoxybenzyl)-pyrimidin-2-yl]-acetimido-acid ethyl ester and 2-sulfanilamido-4-methyl-pyrimidine (sulfamerazine).

17. N-[4-Amino-5-(3,4,5-trimethoxybenzyl)-pyrimidin-2-yl]-N'-(4-sulfonylguanidino)-phenyl-acetamidine of melting point 246° C. from N-[4-amino-5-(3,4,5-trimethoxybenzyl)-pyrimidin-2-yl]-acetimido-acid ethyl ester and 4-aminobenzenesulfonylguanidine (sulfaguanidine).

18. N-[4-Amino-5-(3,4,5-trimethoxybenzyl)-pyrimidin-2-yl]-N'-[4-(5-methyl-isoxazol-3-yl)-sulfonamido]-phenyl-acetamidine of melting point 155° C. from N-[4amino-5-(3,4,5-trimethoxybenzyl)-pyrimidin-2-yl]-acetimido-acid ethyl ester and 3-sulfanilamido-5-methyl-isoxazole (sulfamethoxazole).

19. N-[4-Amino-5-(3,4,5-trimethoxybenzyl)-pyrimidin-2-yl]-N'-[4-(6-methoxy-pyridazin-3-yl)-sulfonamido]-phenyl-acetamidine of melting point 168° C. from N-[4-amino-5-(3,4,5-trimethoxybenzyl)-pyrimidin-2yl]-acetimido-acid ethyl ester and 3-sulfanilamido-6-methoxy-pyridazine (sulfamethoxypyridazine).

20. N-[4-Amino-5-(3,4,5-trimethoxybenzyl)-pyrimidin-2-yl]-N'-[4-(pyridin-2-yl)-sulfonamido]-phenyl-acetamidine of melting point 237° C. from N-[4-amino-5-(3,4,5-trimethoxybenzyl)-pyrimidin-2-yl]-acetimido-acid ethyl ester and 2-sulfanilamido-pyridine (sulfapyridine).

21. N-[4-Amino-5-(3,4,5-trimethoxybenzyl)-pyrimidin-2-yl]-N'-[4-(4-isopropyl-pyrimidin-2-yl)-sulfonamido]-phenyl-acetamidine of melting point 201° C. from N-[4-amino-5-(3,4,5-trimethoxybenzyl)-pyrimidin-2-yl]-acetimido-acid ethyl ester and 2-sulfanilamido-4-isopropyl-pyrimidine.

22. N-[4-Amino-5-(3,4,5-trimethoxybenzyl)-pyrimidin-2-yl]-N'-[4-(3-methoxy-pyrazin-2-yl)-sulfonamido]-phenyl-acetamidine of melting point 148° C. (with decomposition) from N-[4-amino-5-(3,4,5-trimethoxybenzyl)-pyrimidin-2-yl]-acetimido-acid ethyl ester and 2-sulfanilamido-3-methoxypyrazine (sulfamethoxypyrazine, sulfalene).

Examples of pharmaceutical formulations.
23.
400 mg of 2-sulfanilamido-4,5-dimethyloxazole
80 mg of N-[4-amino-5-(3,4,5-trimethoxybenzyl)-pyrimidin-2-yl]-N'-benzyl-acetamidine (Example 7)
20 mg of corn starch
10 mg of gelatin
8 mg of talc
2 mg of magnesium stearate
20 mg of Primojel The active ingredients are mixed with corn starch and granulated, using the aqueous gelatin solution. The dry granules are seived and mixed with the additives. This mixture is tableted in the conventional manner.
24.
160 mg of 2-sulfanilamido-5-methoxy-pyrimidine
80 mg of N-[4-amino-5-(3,4,5-trimethoxybenzyl)-pyrimidin-2-yl]-N'-phenyl-acetamidine (Example 2)
5 mg of gelatin
30 mg of corn starch
4 mg of talc
1 mg of magnesium stearate The active ingredients are granulated, using the aqueous gelatin solution, and the dried granules are mixed with corn starch, talc and magnesium stearate. This mixture is tableted in the conventional manner.
25.
400 mg of N-[4-amino-5-(3,4,5-trimethoxybenzyl)-pyrimidin-2-yl]-N'-[4-pyrimidin-2-yl)-sulfonamido]-phenyl-acetamidine (Example 15)
20 mg of corn starch
10 mg of gelatin 8 mg of talc
2 mg of magnesium stearate
20 mg of Primojel The active ingredient is mixed with corn starch and granulated, using the aqueous gelatin solution. The dry granules are sieved and mixed with the additives. This mixture is tableted in the conventional manner.
26.
250 mg of N[4-amino-5-(3,4,5-trimethoxybenzyl)-pyrimidin-2-yl]-N'-[4-(5-methoxy-pyrimidin-2-yl)-sulfonamido]-phenyl-acetamidine (Example 13)
5 mg of gelatin
30 mg of corn starch
4 mg of talc
1 mg of magnesium stearate The active ingredient is granulated, using the aqueous gelatin solution, and the dried granules are mixed with corn starch, talc and magnesium stearate. This mixture is tableted in the conventional manner.
27.
4.00 g of 2-sulfanilamido-5-methoxy-pyrimidine
2.00 g of N-[4-amino-5-(3,4,5-trimethoxybenzyl)-pyrimidin-2-yl]-N',N'-dimethyl-acetamidine (Example 3)
1.9 of Tylose C 30
30.0 g of sugar
10.0 g of glycerol
2.5 g of bentonite
0.06 g of flavoring
0.04 g of Nipagin M
0.06 g of Nipasol sodium
ad 100.00 g demineralized water The very finely milled active ingredients are suspended in the aqueous Tylose mucilage. All the other ingredients are then added successively, whilst stirring. Finally, the mixture is made up to 100.0 g with water.
28.
0.300 g of N-[4-amino-5-(3,4,5-trimethoxybenzyl)-pyrimidin-2-yl]-N'-[4-(5-methyl-pyrimidin-2-yl)-sulfonamido]-phenyl-acetamidine (Example 14)
1.9 g of Tylose C 30
30.0 g of sugar
10.0 g of glycerol
2.5 g of bentonite
0.06 g of flavoring
0.04 g of Nipagin M
0.06 g of Nipasol sodium
ad 100.00 g demineralized water The very finely milled active ingredient is suspended in the aqueous Tylose mucilage. All the other ingredients are then added successively, whilst stirring. Finally, the mixture is made up to 100.0 g with water.

We claim:
1. An amidino-benzylpyrimidine of the formula I

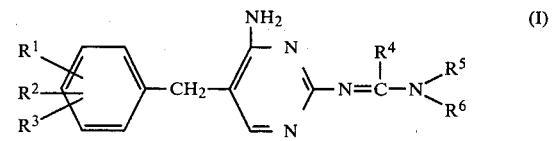

where $R^1$, $R^2$, and $R^3$, which may be identical or different, are hydrogen, methyl, methoxy or chlorine, $R^4$ is alkyl of 1 to 6 carbon atoms or benzyl and $R^5$ and $R^6$, which may be identical or different, are hydrogen, lower alkyl of 1 to 4 carbon atoms, or phenyl, trimethoxybenzyl, cyclohexyl, adamantyl or furfuryl, or one of the radicals $R^5$ and $R^6$ is —$C_6H_4$—$SO_2$—NH—$R^7$, where $R^7$ is

or, pyrimidin-2-yl, 4-methyl-pyrimidin-2-yl, 5-methyl-pyrimidin-2-yl, 5-isopropyl-pyrimidin-2-yl, 5-methoxy-pyrimidin-2-yl, 6-methoxy-pyridazin-3-yl, 3-methoxy-pyrazin-2-yl, 5-methyl-isoxazol-3-yl or 2-pyridinyl, or $R^5$ and $R^6$ together with the nitrogen to which they are bonded are a saturated heterocyclic ring of 5–7 members containing one oxygen atom or one $>$N—Y group, where Y is methyl, benzyl or phenyl, and their pharmacologically acceptable salts with acids.

2. A compound of the formula I as claimed in claim 1, where $R^4$ is lower alkyl of 1 to 4 carbon atoms or benzyl, and $R^5$ and $R^6$, which may be identical or different, are hydrogen, lower alkyl of 1 to 4 carbon atoms, trimethoxybenzyl, benzyl or phenyl, or together are polymethylene of 4 or 5 methylene groups, which may be interrupted by oxygen or $>$N—Y, where Y is methyl, benzyl or phenyl, or $R^5$ is hydrogen and $R^6$ is —$C_6H_4$—$SO_2NH$—$R^7$, where $R^7$ is

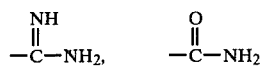

or pyrimidin-2-yl, 4-methyl-pyrimidin-2-yl, 5-methyl-pyridimin-2-yl, 5-isopropyl-pyrimidin-2-yl, 5-methoxy-pyridimin-2-yl, 6-methoxy-pyridazin-3-yl, 3-methoxy-pyrazin-2-yl, 5-methyl-isoxazol-3-yl or 2-pyridinyl.

3. N-[4-Amino-5-(3,4,5-trimethoxybenzyl)-pyrimidin-2-yl]-acetamidine and its pharmacologically acceptable salts with acids.

4. N-[4-Amino-5-(3,4,5-trimethoxybenzyl)-pyrimidin-2-yl]-N'-phenyl-acetamidine and its pharmacologically acceptable salts with acids.

5. N-[4-Amino-5-(3,4,5-trimethoxybenzyl)-pyrimidin-2-yl]-N',N'-dimethyl-acetamidine and its pharmacologically acceptable salts with acids.

6. N-[4-Amino-5-(3,4,5-trimethoxybenzyl)-pyrimidin-2-yl]-N',N'-diethyl-acetamidine and its pharmacologically acceptable salts with acids.

7. N-[4-Amino-5-(3,4,5-trimethoxybenzyl)-pyrimidin-2-yl]-N',N'-(3-aza-3-phenyl-pentamethylene)-acetamidine and its pharmacologically acceptable salts with acids.

8. N-[4-Amino-5-(3,4,5-trimethoxybenzyl)-pyrimidin-2-yl]-N',N'-tetramethylene-acetamidine and its pharmacologically acceptable salts with acids.

9. N-[4-Amino-5-(3,4,5-trimethoxybenzyl)-pyrimidin-2-yl]-N'-benzyl-acetamidine and its pharmacologically acceptable salts with acids.

10. N-[4-Amino-5-(3,4,5-trimethoxybenzyl)-pyrimidin-2-yl]-N'-(3,4,5-trimethoxybenzyl)-acetamidine and its pharmacologically acceptable salts with acids.

11. N-[4-Amino-5-(3,4,5-trimethoxybenzyl)-pyrimidin-2-yl]-N',N'-(3-oxa-pentamethylene)-acetamidine and its pharmacologically acceptable salts with acids.

12. N-[4-Amino-5-(3,4,5-trimethoxybenzyl)-pyrimidin-2-yl]-N'-furfuryl-acetamidine and its pharmacologically acceptable salts with acids.

13. N-[4-Amino-5-(3,4,5-trimethoxybenzyl)-pyrimidin-2-yl]-N'-cyclohexyl-acetamidine and its pharmacologically acceptable salts with acids.

14. N-[4-Amino-5-(3,4,5-trimethoxybenzyl)-pyrimidin-2-yl]-N'-adamantyl-acetamidine and its pharmacologically acceptable salts with acids.

15. N-[4-Amino-5-(3,4,5-trimethoxybenzyl)-pyrimidin-2-yl]-N'-[4-(5-methoxypyrimidin-2-yl)-sulfonamido]-phenyl-acetamidine and its pharmacologically acceptable salts with acids.

16. N-[4-Amino-5-(3,4,5-trimethoxybenzyl)-pyrimidin-2-yl]-N'-[4-(5-methyl-pyrimidin-2-yl)-sulfonamido]-phenyl-acetamidine and its pharmacologically acceptable salts with acids.

17. N-[4-Amino-5-(3,4,51-trimethoxybenzyl)-pyrimidin-2-yl]-N'-[4-(pyrimidin-2-yl)-sulfonamido]-phenyl-acetamidine and its pharmacologically acceptable salts with acids.

18. N-[4-Amino-5-(3,4,5-trimethoxybenzyl)-pyrimidin-2-yl]-N'-[4-(4-methyl-pyrimidin-2-yl)-sulfonamido]-phenyl-acetamidine and its pharmacologically acceptable salts with acids.

19. N[4-Amino-5-(3,4,5-trimethoxybenzyl)-pyrimidin-2-yl]-N'-(4-sulfonylguanidino)-phenyl-acetamidine and its pharmacologically acceptable salts with acids.

20. N-[4-Amino-5-(3,4,5-trimethoxybenzyl)-pyrimidin-2-yl]-N'-[4-(5-methyl-isoxazol-3-yl)-sulfonamido]-phenyl-acetamidine and its pharmacologically acceptable salts with acids.

21. N-[4-Amino-5-(3,4,5-trimethoxybenzyl)-pyrimidin-2-yl]-N'-[4-(6-methoxy-pyridazin-3-yl)-sulfonamido]-phenyl-acetamidine and its pharmacologically acceptable salts with acids.

22. N-[4-[Amino-5-(3,4,5-trimethoxybenzyl)-pyrimidin-2-yl]-N'-[4-(pyridin-2-yl)-sulfonamido]-phenyl-acetamidine and its pharmacologically acceptable salts with acids.

23. N-[4-Amino-5-(3,4,5-trimethoxybenzyl)-pyrimidin-2-yl]-N'-[4-(4-isopropyl-pyrimidin-2-yl)-sulfonamido]-phenyl-acetamidine and its pharmacologically acceptable salts with acids.

24. N-4-Amino-5-(3,4,5-trimethoxybenzyl)-pyrimidin-2-yl-N'-[4-(3-methoxy-pyrazin-2-yl)-sulfonamido]-phenyl-acetamidine and its pharmacologically acceptable salts with acids.

25. An antibacterial and antiprotozoal composition consisting essential of a pharmaceutically acceptable carrier or excipient and a therapeutically active amount of a compound of claim 1.

\* \* \* \* \*